United States Patent [19]

Schubert et al.

[11] Patent Number: 5,612,094
[45] Date of Patent: Mar. 18, 1997

[54] COMPOSITIONS AND METHODS FOR PRESERVING WOOD PRODUCTS

[75] Inventors: David M. Schubert; Mark J. Manning, both of Los Angeles, Calif.

[73] Assignee: U.S. Borax Inc., Valencia, Calif.

[21] Appl. No.: 544,903

[22] Filed: Oct. 18, 1995

[51] Int. Cl.$^6$ ............................... A01N 3/00; A01N 59/14
[52] U.S. Cl. .................. 427/397; 106/15.05; 106/18.13; 106/18.3; 424/617; 424/657; 424/658; 424/659; 424/660; 427/297; 427/427; 427/440; 428/537.1
[58] Field of Search ............................... 106/18.13, 18.3, 106/15.05; 428/537.1; 427/397, 297, 427, 440; 424/657, 658, 659, 660, 617

[56] References Cited

U.S. PATENT DOCUMENTS

| | | | |
|---|---|---|---|
| 3,183,118 | 5/1965 | Conner | 427/389.9 |
| 3,291,635 | 12/1966 | Conner | 427/390 |
| 3,306,765 | 2/1967 | DuFresne et al. | 428/541 |
| 4,097,430 | 6/1978 | Phillips | 524/43 |
| 4,274,972 | 6/1981 | Sherif et al. | 252/8.6 |
| 4,303,726 | 12/1981 | Turner | 427/297 |
| 4,461,721 | 7/1984 | Goettsche et al. | 106/18.3 |
| 4,661,157 | 4/1987 | Beauford et al. | 106/18.3 |

FOREIGN PATENT DOCUMENTS

| | | | |
|---|---|---|---|
| 2114003 | 8/1983 | United Kingdom | 106/18.13 |

OTHER PUBLICATIONS

Koshimoro, Chemical Abstracts, vol. 100, 54052 (Japan Kokai Tokkyo Koho JP 58, 164, 673) (Sep. 1983).

Svares, Chemical Abstracts, vol. 75, 75338 (U.S.S.R. 283, 546) (Oct. 1970).

Ota et al., Chemical Abstracts, vol. 108, 169476 (Japan, Kokai Tokkyo Koho JP 62, 275, 703) (Nov. 1987).

Supplement to Mellor's Comprehensive Treatise on Inorganic and Theoretical Chemistry, vol. V, Part A, pp. 618–619 (1980) no month.

Magnesium Elektron, ZAA, Data Sheet 721 no date.

Magnesium Elektron, Zirmel 1000, Data Sheet 715 no date.

Magnesium Elektron, Bacote 20, Data Sheet 722 (Feb. 1991).

Magnesium Elektron, Z–Plex 9000, Data Sheet 9000 (Provisional) no date.

Conner et al., Textile Chemist and Colorist, vol. 10, No. 4, pp. 70–74, Apr. 1978.

*Primary Examiner*—Anthony Green
*Attorney, Agent, or Firm*—James R. Thornton

[57] ABSTRACT

Lumber, plywood and other wood products are preserved from attack by fungi, termites and wood-destroying insects as well as fire and flame by treatment with a novel zirconium borate-containing preservative composition. The preservative can be formed by combination of a source of boron such as boric acid and the water-soluble salts thereof with a water-soluble zirconium salt. The $ZrO_2:B_2O_3$ weight ratio in the preservative composition is in the range of from about 0.75:1 to about 10:1.

18 Claims, No Drawings

COMPOSITIONS AND METHODS FOR PRESERVING WOOD PRODUCTS

This invention relates to the preservation of wood and more particularly, this invention provides novel compositions and methods for preserving wood products, such as lumber, plywood, poles, railroad crossties and the like, by use of borate based preservative and fire-retardant compositions combined with soluble zirconium salts.

BACKGROUND OF THE INVENTION

Inorganic boron compounds have been used as wood preservatives and fire retardants for many years. The basic materials, boric acid and borax, are readily available, inexpensive and relatively harmless to humans, and their toxicity to fungi, termites, and wood-destroying insects has been clearly established. At higher levels of treatment, the borates are also effective as fire-retardants for lumber and other wood products. However, since the commonly used borates are readily soluble in water, their use has been restricted to applications where leaching is not likely to occur, such as by rain water or soil moisture. In order to alleviate this limitation, various means for insolubilizing or fixing the borate in the wood have been proposed. For example, Du Fresne et al., U.S. Pat. No. 3,306,765, shows impregnation of wood with a mixture of sodium silicate and borax and then treatment with carbon dioxide under pressure to fix the fireproofing agents against leaching. See also USSR Patent 283,546 (Chemical Abstracts 75,75338) and Japanese Kokai Tokkyo Koho 62,275,703 (Chemical Abstracts 108, 169476) which propose treating with a soluble borate-containing preservative and then altering the pH such as with ammonia to precipitate insoluble preservatives in the wood.

Water-soluble zirconium salts are known and have various uses such as for insolubilizing starch binders used in paper coating compositions and to impart thixotropy to dispersions of polymers such as emulsion paints. See Phillips U.S. Pat. No. 4,097,430. Water-insoluble salts of metals such as copper, mercury and nickel are known to be fungicidal and can be solubilized by mixing with zirconyl acetate in acetic acid solution or with zirconyl ammonium carbonate solutions to provide compositions for rendering cotton fabric rot-resistant. See Conner, U.S. Pat. Nos. 3,183,118 and 3,291,635. Copper borate and phenyl mercury borate are among the metal salts that may be used. For example, cotton fabric can be treated with solubilized copper borate and then cured, such as by heating at 145° C., to convert the soluble form to an insoluble form. Subsequently, Conner et al. substituted copper carbonate for copper borate. See *Textile Chemist and Colorist,* April 1978, and see Sherif et al. U.S. Pat. No. 4,274,972, which claims a process for preparing an improved dilute aqueous copper zirconium ammonium carbonate solution, having enhanced resistance to gelation.

Japanese Kokai Tokkyo Koho 58,164,673 (1983)(Chemical Abstracts, Vol. 100, 54052) describes preparation of a fireproofing agent from a mixture of acidified shellfish fossils and siliceous soil with a solution of boric acid, borax and zirconium silicate.

Although a simple zirconium borate has not been well-defined, anhydrous and hydrated zirconium borates are reviewed in Supplement to Mellor's Comprehensive Treatise on Inorganic and Theoretical Chemistry, Volume V, Part A, Pages 618–619 (1980).

SUMMARY OF THE INVENTION

The present invention provides novel aqueous borate preservative compositions for wood products comprising an aqueous solution of 1) a source of boron selected from the group consisting of boric acid and the water-soluble salts thereof and 2) a water-soluble zirconium salt, wherein the $ZrO_2:B_2O_3$ weight ratio in said preservative composition is about 0.75:1 to 10:1. There are also provided methods for preserving wood products which comprise treating the wood products with the aqueous borate preservative according to this invention. Preservation includes protection against fire as well as controlling fungi, termites and wood-destroying insects.

DETAILED DESCRIPTION OF THE INVENTION

The preservative compositions of this invention are prepared by admixing one or more of the boron compounds with the zirconium salt in an aqueous solution. Alternatively, the compositions may be formed within the lumber products to be protected. For example, the lumber product can be treated first with a solution of the zirconium salt and then treated with an aqueous solution of the boron compound, thereby forming the preservative composition within the structure of the wood. However, it is preferred that the preservative composition is formed prior to treatment of the wood.

In the preparation of the preservative compositions, the source of boron is combined with the water-soluble zirconium salt, such as in an aqueous solution. For example, one or more of the boron compounds may be dissolved in an aqueous solution of the zirconium salt or a solution of boron compound may be combined with a solution of the zirconium salt. The amount of boron compound and zirconium salt is adjusted so that the resultant preservative composition has a $ZrO_2:B_2O_3$ weight ratio of from about 0.75:1 to about 10:1, preferably from about 1.5:1 to about 3.5:1. The resultant preservative compositions may be diluted, if desired, prior to use as a wood treatment, or they may be used in concentrated form.

The source of boron can be one or more of boric acid and/or the water-soluble salts of boric acid, such as sodium tetraborate decahydrate (borax), sodium tetraborate pentahydrate, sodium octaborate tetrahydrate, sodium metaborate, sodium perborate hydrates, potassium tetraborate, sodium pentaborate, ammonium pentaborate hydrate, anhydrous sodium tetraborate, potassium metaborate, and the like. Preferably, the boron compound is sodium octaborate tetrahydrate or a mixture of boric acid and sodium tetraborate pentahydrate. Sodium octaborate tetrahydrate is commercially available as TIM-BOR® wood preservative from U.S. Borax Inc., Valencia, Calif.

The zirconium salt may be any of the water-soluble zirconium salts, especially the commercially available solutions of zirconium salts such as ammonium zirconium carbonate, zirconium acetate, zirconium propionate, zirconium orthosulfate, potassium zirconium carbonate, zirconium hydroxychloride, zirconium oxychloride, zirconium nitrate, and acidic solutions of zirconium basic carbonate. A particularly useful zirconium salt is commercially available as an aqueous solution of ammonium zirconium carbonate (containing 20% by weight $ZrO_2$) under the name Bacote 20 from Magnesium Elektron Ltd.

In practicing the method of this invention, the wood product is treated with the preservative solution in a manner and with an amount sufficient to impregnate the wood with the preservative solution and deposit an effective amount of preservative in the structure of the wood. The treatment may be by spraying or by merely dipping the wood article in the preservative solution and allowing it to soak for a time sufficient to diffuse the preservative throughout the wood, or the treatment may be under pressure and/or vacuum. The effective amount of preservative in the wood will be dependent upon the nature of the protection desired. For example, if preservation from attack by fungi, termites and wood-destroying insects is desired, the amount of preservative in the wood should be in the range of from about 0.5 to about 2.5% by weight boric acid equivalent (about 0.3 to about 1.5% $B_2O_3$). If preservation from fire is the goal (fire-retardant), an effective amount is in the range of from about 10 to about 15% by weight, boric acid equivalent (about 5 to about 9% $B_2O_3$). After treatment, the wood product is allowed to dry in the air to a constant weight or it may be dried by heating, such as in a kiln, thereby providing a leach-resistant zirconium borate complex in the wood. Preferably, the treated article is heated, such as at a temperature of from about 50° to about 105° C., to accelerate drying and to provide the best leach-resistant properties to the wood.

In an alternative treatment procedure, the wood product may be treated in two steps such as by first treating with the zirconium salt solution and then treating with an aqueous solution of the boron compound. Alternatively, the order of treatments may be reversed. However, the preferred procedure is to treat the wood product with the preformed preservative solution containing the boron-zirconium composition of this invention.

The resultant treated wood products are preserved against the ravages of fungi, termites, and wood destroying insects, and if a sufficient amount of preservative is employed, is resistant to fire. The preservative is "fixed" in the wood product and is therefore resistant to leaching by moisture, making it especially useful for outdoor or ground contact service such as decking, utility poles, exterior siding, outdoor furniture, etc.

The following examples illustrate the novel preservative compositions and the methods of this invention

EXAMPLE I

Sodium octaborate tetrahydrate (20 g.) was dissolved in 500 g. of an aqueous solution of ammonium zirconium carbonate containing 20% by weight $ZrO_2$ (Bacote 20) and 480 g. of deionized water. Bacote 20 is a commercially available aqueous solution which nominally contains 20% $ZrO_2$, 8% $NH_3$, and 13% $CO_2$, all by weight. The resulting solution contained 2.0% of sodium octaborate (1.34% $B_2O_3$) and 10% zirconium oxide.

EXAMPLE II

Ammonium pentaborate (10 g.) and 50 g. of Bacote 20 ammonium zirconium carbonate solution were combined in 40 g. of deionized water to give 100 g. of a clear solution containing 10% of $ZrO_2$ and 6.4% of $B_2O_3$.

EXAMPLE III

Ammonium pentaborate (39.09 g.) and 125.0 g. of Bacote 20 ammonium zirconium carbonate solution were combined with 85.91 g. of deionized water to give 250 g. of a clear solution containing 10% $ZrO_2$ and 10% $B_2O_3$.

EXAMPLES IV–X

A series of seven wood preserving solutions were prepared from boric acid and ammonium zirconium carbonate by dissolving 8.88 grams of boric acid in varying amounts of Bacote 20 ammonium zirconium carbonate solution which had been diluted with deionized water. Effervescence was noted in each case when the boric acid was added to the solutions, indicating the evolution of carbon dioxide gas. The resultant solutions contained 5% $B_2O_3$ and from 2.5 to 17.5% $ZrO_2$ and had a $ZrO_2/B_2O_3$ ratio ranging from 0.5 to 3.5. The pH of the solutions ranged from 7.25 to 8.73. Each solution was placed in an evaporating dish and allowed to evaporate down to dryness at room temperature. After two weeks the remaining residue of each solution was a clear, glassy solid, which formed either a monolith or cracked into a few solid fragments. Samples of the clear solid residues were heated at 105° C. overnight to give opaque glasses. The opaque glasses were ground to fine powders using a shatter box and a 5.00 g. sample of each powder was placed in a 100 ml. soda lime (non-borosilicate) glass jar. Based on the compositions of the starting solutions, these 5.00 g. samples were calculated to have the following compositions.

TABLE 1

| Example | % $B_2O_3$ | g $B_2O_3$ | $ZrO_2/B_2O_3$ Weight Ratio |
|---------|-----------|------------|-----------------------------|
| IV      | 38.6      | 1.93       | 0.5                         |
| V       | 29.7      | 1.48       | 1.0                         |
| VI      | 23.8      | 1.19       | 1.5                         |
| VII     | 19.8      | 0.99       | 2.0                         |
| VIII    | 17.0      | 0.85       | 2.5                         |
| IX      | 15.1      | 0.76       | 3.0                         |
| X       | 13.6      | 0.68       | 3.5                         |

Deionized water (45.00 g.) was added to each jar to make 10% by weight glass powder slurries. The jars were sealed and allowed to stand at room temperature for 26 days. Each day, the slurries were shaken to resuspend the solids in each jar. At the end of the 26 day test period, the solids were separated by filtration and the clear supernatant solutions were analyzed for borate content to determine the amount of borate that had leached out of the glasses. The following results were obtained as shown in Table 2.

TABLE 2

| Example | g $B_2O_3$ in Sample | % $B_2O_3$ in Leachate | g $B_2O_3$ Leached | % $B_2O_3$ Leached |
|---------|----------------------|------------------------|--------------------|--------------------|
| IV      | 1.93                 | 3.57                   | 1.78               | 92.0               |
| V       | 1.48                 | 2.04                   | 1.02               | 68.9               |
| VI      | 1.19                 | 1.36                   | 0.68               | 57.1               |
| VII     | 0.99                 | 1.06                   | 0.50               | 50.5               |
| VIII    | 0.85                 | 0.85                   | 0.42               | 49.4               |
| IX      | 0.76                 | 0.81                   | 0.40               | 52.6               |
| X       | 0.68                 | 0.71                   | 0.36               | 52.9               |

Although a portion of the borate was leached from the samples under the rigorous test conditions, a substantial amount of borate remained, especially at the preferred $ZrO_2:B_2O_3$ ratios of from about 1.5:1 to about 3.5:1. Accordingly, a substantial amount of borate would remain in the dried preservative composition under very rigorous leaching conditions such as by constant rain or water immersion over a long period of time.

EXAMPLE XI–XIII

Sodium octaborate tetrahydrate (40 g.) was dissolved in each of three samples containing 200, 500 and 1000 grams of Bacote 20 ammonium zirconium carbonate solution which had been diluted with sufficient deionized water to give 2000 g. of a final solution containing 2.0% by weight sodium octaborate (1.34% $B_2O_3$) and 2%, 5% and 10%, respectively, by weight of $ZrO_2$. The pH of the resultant clear solutions was 8.82, 9.05 and 9.23, respectively. The solutions were used to pressure treat southern yellow pine cubes according to the following procedure, in which Example XI contained 2% $ZrO_2$, Example XII contained 5% $ZrO_2$ and Example XIII contained 10% $ZrO_2$. Each example also contained 1.34% $B_2O_3$.

Cubes (¾ inch) of Southern Yellow Pine were pressure treated with the ammonium zirconium borate solutions by placing the cubes in a tray and weighting them down with plastic coated lead weights. The treating solutions were then poured into the container, completely covering all the cube samples. The treating cycle consisted of a short vacuum cycle (5 minutes at 28" Hg) followed by a 30 minute pressure cycle at 140 psi. The samples were weighed initially and then again following pressure treatment; chemical retentions were then calculated using the weight difference and solution concentration. The treated samples were dried by heating in a 50° C. oven for about 24 hours.

Leach tests were performed according to the procedure of the American Wood Preservers' Association Standard E11-87: Standard Method of Determining the Leachability of Wood Preservatives. The treated samples were vacuum impregnated with distilled water (28" Hg for 20 minutes) and a sample of the resulting solution taken and analyzed for boron to obtain leach results after the 20 minute treatment. The initial solution was discarded and the saturated wood samples were submerged in fresh distilled water. Periodically up to 240 hours, samples of leachate were removed and then the samples were again submerged in fresh distilled water. The collected samples were all analyzed for boron using Inductively Coupled Plasma-Atomic Emission Spectroscopy (ICP-AES). The results are shown in the following Table A.

TABLE A

| Sample Number | Leach Time (Hours) | Example XI | Example XII | Example XIII |
|---|---|---|---|---|
| | | Percent of Initial Boron Content Retained in Cubes After Leaching | | |
| 1 | 0.33 | 87 | 94 | 97 |
| 2 | 2 | 74 | 89 | 95 |
| 3 | 4 | 65 | 84 | 92 |
| 4 | 24 | 35 | 60 | 77 |
| 5 | 29 | 28 | 54 | 74 |
| 6 | 53 | 18 | 40 | 66 |
| 7 | 77 | 12 | 31 | 59 |
| 8 | 146 | 7 | 18 | 47 |
| 9 | 191 | 6 | 13 | 42 |
| 10 | 240 | 5 | 9 | 37 |

The tests were repeated using small coupons of the wood with nominal dimensions of ⅝" thick×4" long×1.5" wide. The procedure was the same except samples of leachate were taken and analyzed up to a total of 1582 hours (66 days) and each treatment was replicated. The following results were obtained as shown in Table B in which the replicates are identified as A an B.

TABLE B

Percent of Initial Boron Content Retained in Cubes After Leaching

| Sample Number | Leach Time (Hours) | Example XI (A) | Example XI (B) | Example XII (A) | Example XII (B) | Example XIII (A) | Example XIII (B) |
|---|---|---|---|---|---|---|---|
| 1 | 0.33 | 92 | 92 | 98 | 98 | 99 | 99 |
| 2 | 2 | 85 | 85 | 95 | 95 | 97 | 97 |
| 3 | 4 | 81 | 81 | 93 | 93 | 96 | 96 |
| 4 | 23 | 65 | 65 | 80 | 81 | 90 | 90 |
| 5 | 28 | 62 | 62 | 78 | 78 | 89 | 88 |
| 6 | 46 | 55 | 55 | 70 | 71 | 84 | 84 |
| 7 | 76 | 46 | 46 | 59 | 60 | 77 | 76 |
| 8 | 100 | 41 | 41 | 52 | 53 | 71 | 70 |
| 9 | 169 | 31 | 32 | 41 | 40 | 60 | 58 |
| 10 | 214 | 27 | 28 | 36 | 35 | 54 | 52 |
| 11 | 263 | 25 | 26 | 31 | 31 | 49 | 48 |
| 12 | 336 | 22 | 23 | 27 | 26 | 44 | 42 |
| 13 | 700 | 19 | 20 | 22 | 20 | 36 | 37 |
| 14 | 1032 | 17 | 18 | 19 | 17 | 31 | 33 |
| 15 | 1582 | 16 | 17 | 16 | 14 | 26 | 28 |

EXAMPLE XIV

Boric acid (23.98 grams; 0.39 mole) was dissolved in 476.02 grams of deionized water and this solution was then added to 500 grams of Bacote 20 ammonium zirconium carbonate solution. The resultant 1000 grams of clear solution contained 1.35% by weight $B_2O_3$ and 10% by weight $ZrO_2$.

EXAMPLE XV

Boric acid (24.78 grams; 0.40 mole) was dissolved in 490.0 grams of deionized water and this solution was then added to 512 grams of zirconium acetate solution containing 22% $ZrO_2$. The resultant 1026.8 grams of clear solution contained 1.35% by weight $B_2O_3$ and 11% by weight $ZrO_2$.

EXAMPLE XVI

Sodium octaborate tetrahydrate (20 g.) was dissolved in 500 g. of a clear, alkaline aqueous solution of potassium zirconium carbonate containing about 20% by weight $ZrO_2$ (commercially available as Zirmel 1000) and 480 g. of deionized water. The resulting clear solution contained 2% of sodium octaborate (1.34% $B_2O_3$) and 10% zirconium oxide.

Various changes and modifications of the invention can be made and, to the extent that such variations incorporate the spirit of this invention, they are intended to be included within the scope of the appended claims.

What is claimed is:

1. An aqueous borate preservative composition for wood products comprising an aqueous solution of 1) a source of boron selected from the group consisting of boric acid and the water-soluble salts thereof and 2) a water-soluble zirconium salt, in which the $ZrO_2:B_2O_3$ weight ratio is about 0.75:1–10:1 and which, upon drying, said preservative composition forms a zirconium borate complex which is resistant to leaching by moisture.

2. An aqueous borate preservative composition according to claim 1 in which said water-soluble zirconium salt is selected from the group consisting of ammonium zirconium carbonate, zirconium acetate, zirconium propionate, zirconium orthosulfate, potassium zirconium carbonate and acidic solutions of zirconium basic carbonate.

3. An aqueous borate preservative composition according to claim 1 in which said source of boron is a sodium borate.

4. An aqueous borate preservative composition according to claim 1 in which said source of boron is boric acid.

5. A aqueous borate preservative composition according to claim 1 in which said $ZrO_2:B_2O_3$ weight ratio is about 1.5:1 to 3.5:1.

6. An aqueous borate preservative composition for wood products comprising an aqueous solution of sodium octaborate tetrahydrate and ammonium zirconium carbonate, in which the $ZrO_2:B_2O_3$ weight ratio is about 0.75:1–10:1.

7. The method for preserving wood products against fungi, insects and fire, which comprises treating said wood product with a fungicidal, insecticidal and fire-retardant amount of 1) a borate selected from the group consisting of boric acid and the water-soluble salts thereof and 2) a water-soluble zirconium salt, and drying said treated wood product, thereby depositing in said wood product a zirconium borate complex which is resistant to leaching by moisture, wherein the $ZrO_2:B_2O_3$ weight ratio is about 0.75:1 to 10:1 and wherein the resultant preserved wood product contains about 0.3 to about 9% by weight $B_2O_3$.

8. The method according to claim 7 in which said $ZrO_2:B_2O_3$ weight ratio is about 1.5:1 to 3.5:1.

9. The method according to claim 7 in which a zirconium borate complex, which is resistant to leaching by water, is formed in said wood product.

10. The method according to claim 7 in which said wood product is dried by heating at a temperature in the range of from about 50° C. to about 105° C.

11. The method according to claim 7 in which said wood product is treated by soaking in an aqueous preservative solution comprising said source of boron and said water-soluble zirconium salt for a period of time sufficient to diffuse said preservative solution throughout said wood product.

12. The method according to claim 7 in which said wood product is treated with an aqueous preservative solution comprising said source of boron and said water-soluble zirconium salt under pressure so as to distribute said preservative solution throughout said wood product.

13. The method according to claim 7 in which a fire-retardant amount of said zirconium borate complex is deposited in said wood product.

14. The method according to claim 7 in which an insecticidal amount of said zirconium borate complex is deposited in said wood product.

15. Wood products containing an insecticidal and fire-retardant amount of a zirconium borate preservative which is resistant to leaching by water.

16. Wood products according to claim 15 containing from about 0.3 to about 9% by weight $B_2O_3$.

17. A fire-retardant wood product containing a fire-retardant amount of a zirconium borate complex which is resistant to leaching by water, said wood product containing about 5 to about 9% by weight $B_2O_3$.

18. A wood product which is resistant to attack by fungi and insects, containing an insecticidal amount of a zirconium borate complex in which the $ZrO_2:B_2O_3$ weight ratio is about 0.75:1 to 10:1.

\* \* \* \* \*